United States Patent
Kwak et al.

(10) Patent No.: US 11,390,582 B2
(45) Date of Patent: Jul. 19, 2022

(54) POLYMORPHS OF 1-(4-BENZYLOXY-BENZYL)-3-METHYL-THIOUREA

(71) Applicants: Seoul National University R&DB Foundation, Seoul (KR); Therasid Bioscience Inc., Gyeonggi-do (KR)

(72) Inventors: Wooyoung Kwak, Gyeonggi-do (KR); Sungki Seo, Seoul (KR); Heung Jae Kim, Gyeonggi-do (KR)

(73) Assignees: Therasid Bioscience Inc., Gyeonggi-Do (KR); Seoul National University R&DB Foundation, Seoul (KR)

( * ) Notice: Subject to any disclaimer, the term of this patent is extended or adjusted under 35 U.S.C. 154(b) by 227 days.

(21) Appl. No.: 16/696,343

(22) Filed: Nov. 26, 2019

(65) Prior Publication Data

US 2021/0155586 A1    May 27, 2021

(51) Int. Cl.
*C07C 335/12*        (2006.01)

(52) U.S. Cl.
CPC ........ *C07C 335/12* (2013.01); *C07B 2200/13* (2013.01)

(58) Field of Classification Search
CPC combination set(s) only.
See application file for complete search history.

(56) References Cited

U.S. PATENT DOCUMENTS

2018/0265462 A1    9/2018   Lee et al.

OTHER PUBLICATIONS

Park, Yohan, et al., "N-Methylthioureas as New Agonists of Retinoic Acid Receptor-Related Orphan Receptor", Arch. Pharm. Res., vol. 35, No. 8, pp. 1393-1401 (2012).

*Primary Examiner* — Kathrien A Cruz

(74) *Attorney, Agent, or Firm* — Servilla Whitney LLC

(57) ABSTRACT

The present disclosure relates to a 1-(4-benzyloxy-benzyl)-3-methyl-thiourea compound in crystalline forms A, B, C, or amorphous form, a method for preparing the compound in the crystalline or amorphous forms, and a use of the compound for preventing or treating a metabolic disease or inflammatory disease.

15 Claims, 10 Drawing Sheets

POLYMORPHS OF 1-(4-BENZYLOXY-BENZYL)-3-METHYL-THIOUREA

TECHNICAL FIELD

The present disclosure relates a 1-(4-benzyloxy-benzyl)-3-methyl-thiourea compound in crystalline forms A, B, C, or amorphous form, a method for preparing the compound in the crystalline or amorphous form, and a use of the compound for preventing or treating a metabolic disease or inflammatory disease.

BACKGROUND ART

ROR$\alpha$, also known as NR1F1, RORA, or RZR, is a member of the steroid hormone receptor superfamily, and a transcriptional factor regulating gene expression. It is known that the activation of the ROR$\alpha$ gene is useful for preventing or treating a metabolic disease or inflammatory disease.

Compounds of Formula 1, which activate the ROR$\alpha$ gene, are disclosed in Korean Patent No. 10-1450960 and US Patent Publication No. US 2018/0265462 A1.

[Formula 1]

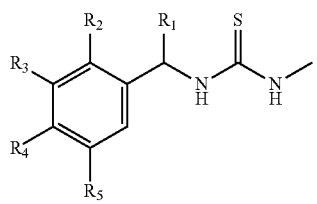

Wherein, $R_1$ is a hydrogen atom or a C1-C3 alkyl group;

$R_2$ is a hydrogen atom, a halogen atom, a C1-C3 alkyl group, a C1-C3 alkoxy group, a nitro group, a hydroxyl group, or a phenoxy group;

$R_3$ is a hydrogen atom, a halogen atom, a C1-C3 alkyl group, a C1-C3 alkoxy group, a nitro group, a hydroxyl group, or a phenoxy group;

$R_4$ is a hydrogen atom, a halogen atom, a C1-C3 alkyl group, a C1-C3 alkoxy group, a nitro group, a hydroxyl group, a cyano group, a dimethylamino group, a methylsulfonylamide group, a trifluoromethyl group, a vinyl benzene group, a phenoxy group, a benzoxy group, a substituted or unsubstituted C6 aryl group, or a phenylamine group wherein the aromatic ring of the substituted C6 aryl group or the phenoxy group is substituted with a C1-C3 alkyl group, a C1-C3 alkoxy group, a trifluoromethyl group, or a t-butyl group; and $R_5$ is a hydrogen atom, a halogen atom, a C1-C3 alkyl group, a C1-C3 alkoxy group, a nitro group, a hydroxyl group, or a phenoxy group, provided that when all of $R_2$ to $R_5$ are a hydrogen atom and when $R_4$ is a methyl group or a chlorine atom, all of $R_2$, $R_3$, and $R_5$ are not a hydrogen atom. In particular, Korean Patent No. 10-1450960 and US Patent Publication No. US 2018/0265462 disclose 1-(4-benzyloxy-benzyl)-3-methyl-thiourea (Formula 2).

[Formula 2]

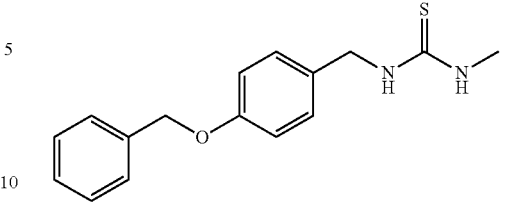

A method for preparing the compound of Formula 1, particularly, 1-(4-benzyloxy-benzyl)-3-methyl-thiourea (Formula 2) is also described in Korean Patent No. 10-1450960 and US Patent Publication No. US 2018/0265462, which are incorporated herein by reference. Further, they are also disclosed in Arch Pharm Res Vol 35, No 8, 1393-1401, 2012. Among the disclosed compounds, a compound of formula 2 exhibits a remarkable effect for the prevention or treatment of a metabolic disease or inflammatory disease.

According to published guidelines or regulations in each country, there are fundamental requirements that pharmacologically active ingredients need to meet. For example, stability of a pharmaceutical ingredient, stability during the preparation of a pharmaceutical formulation, and stability of a pharmaceutical substance in a final pharmaceutical composition are considered. There are various factors that affect the stability of a pharmaceutically active ingredient, but it is well known that the crystalline forms of the active ingredient may have substantially different and pharmaceutically important properties such as an elution and bioavailability, as well as stability. In addition, one form may provide a significantly improved advantage in the preparation process of a solid formulation, such as accurate measurement of an active ingredient, easier filtration, or improved stability during the granulation or storage, as compared to other forms of the same drug. Furthermore, a specific preparation method suitable for one form may provide several advantages such as a solvent or preparation process which is economically feasible or environmentally suitable or a higher purity or higher yield of a desired product, to a manufacturer of an active ingredient.

Until now, a crystalline form for the compound of Formula 2 has not been previously reported. Moreover, in order to remove impurities included in the compound and increase the purity, column purification is performed, which cannot be applied to commercialization for mass production.

Thus, the present inventors have made efforts to obtain a crystalline form of 1-(4-benzyloxy-benzyl)-3-methyl-thiourea (Formula 2) in high purity that is stable for a long period of time and can be applied to commercialization for pharmaceutical use, which have now resulted in preparation of a novel crystalline form of 1-(4-benzyloxy-benzyl)-3-methyl-thiourea (Formula 2) and also confirmed that the crystalline form has improved physical and chemical properties such as storage stability, thereby arriving at the present invention.

Technical Problem

An objective of the present disclosure is to provide crystalline forms A, B, and C, and an amorphous form of 1-(4-benzyloxy-benzyl)-3-methyl-thiourea.

Another objective of the present disclosure is to provide a method for preparing the crystalline forms and the amorphous form.

Solution to Problem

Through constant research to solve the problems above, the present inventors confirmed that different crystalline forms exist. As such, the present disclosure provides polymorphs of 1-(4-benzyloxy-benzyl)-3-methyl-thiourea, and a preparation method thereof.

Specifically, the present disclosure provides crystalline form A of 1-(4-benzyloxy-benzyl)-3-methyl-thiourea, and a preparation method thereof. Crystalline form A exhibits high stability against mechanical and/or storage conditions and aqueous vapor stress.

The present disclosure also provides crystalline forms B and C of 1-(4-benzyloxy-benzyl)-3-methyl-thiourea, and a preparation method thereof.

The present disclosure also provides an amorphous form of 1-(4-benzyloxy-benzyl)-3-methyl-thiourea, and a preparation method thereof.

The compound "1-(4-benzyloxy-benzyl)-3-methyl-thiourea" is referred to as the compound name per se or "Formula 2" herein.

In the following descriptions of the present disclosure, polymorphs exhibit a powder X-ray diffraction (PXRD) pattern having a characteristic peak at a recited position. In one embodiment, it is to be understood that the polymorph exhibits a PXRD pattern having a characteristic peak at a position of a recited diffraction angle $2\theta \pm 0.2°$, along with the intensity (% ($I/I_0$)) value. It is to be noted that the intensity value is included for information only, and the definition of each peak should not be construed as being limited to a specific intensity value.

In one embodiment, the present disclosure relates to a crystalline form of a compound 1-(4-benzyloxy-benzyl)-3-methyl-thiourea capable of exhibiting a powder X-ray diffraction (PXRD) spectrum including characteristic peaks at a diffraction angle $2\theta$ of 16.4, 19.7, 23.1, and 24.5, for example, an essentially pure crystalline form A (FIG. 1). Further, the powder X-ray diffraction (PXRD) spectrum of crystalline form A may further include characteristic peaks at a diffraction angle $2\theta$ of 10.9, 13.5, 15.3, and 27.5, in addition to the previously illustrated peaks. In addition, the powder X-ray diffraction (PXRD) spectrum of crystalline form A may further include characteristic peaks at a diffraction angle $2\theta$ of 16.0, 21.7, 27.1, and 29.5. Alternatively, crystalline form A may exhibit a powder X-ray diffraction (PXRD) spectrum including characteristic peaks at four or more diffraction angles $2\theta \pm 0.2°$ selected from the group consisting of 10.9, 13.5, 15.3, 16.0, 16.4, 19.7, 21.7, 23.1, 24.5, 27.1, 27.5, and 29.5.

Crystalline form A may have an endothermic peak within a range of 120° C. to 130° C. during a differential scanning calorimetry (DSC) analysis at a heating rate of 10° C./min Specifically, crystalline form A has the apex temperature of the endothermic peak within a range of about 123 to 128° C. during the DSC analysis (FIG. 2).

Crystalline form A is not a solvate, that is, crystalline form A of Formula 2 is in a non-solvated form. As used herein, the term "non-solvated form" means that a thermogravimetric analysis (TGA) curve of crystalline form A of Formula 2 exhibits a weight loss of less than about 4 wt %, preferably, a weight loss of less than about 2 wt % at about 100° C. or less (FIG. 3).

In another embodiment, the present disclosure relates to a crystalline form of a compound 1-(4-benzyloxy-benzyl)-3-methyl-thiourea capable of exhibiting a powder X-ray diffraction (PXRD) spectrum including characteristic peaks at a diffraction angle $2\theta$ of 5.9, 11.8, and 17.8, for example, an essentially pure crystalline form B (FIG. 4). Further, the powder X-ray diffraction (PXRD) spectrum of crystalline form B may further include characteristic peaks at a diffraction angle $2\theta$ of 14.8 and 23.8, in addition to the previously illustrated peaks. Alternatively, crystalline form B may exhibit a powder X-ray diffraction (PXRD) spectrum including characteristic peaks at four or more diffraction angles $2\theta \pm 0.2°$ selected from the group consisting of 5.9, 11.8, 14.8, 17.8, and 23.8.

Crystalline form B has the apex temperature of the endothermic peak within a range of 105° C. to 115° C. and a range of 123° C. to 130° C. during a differential scanning calorimetry (DSC) analysis at a heating rate of 10° C./min (FIG. 5).

Crystalline form B is not a solvate, that is, crystalline form B of Formula 2 is in a non-solvated form. A thermogravimetric analysis (TGA) curve of crystalline form B exhibits a weight loss of less than about 4 wt %, preferably, a weight loss of less than about 2 wt % at about 100° C. or less (FIG. 6).

In still another embodiment, the present disclosure relates to a crystalline form of a compound 1-(4-benzyloxy-benzyl)-3-methyl-thiourea capable of exhibiting a powder X-ray diffraction (PXRD) spectrum including characteristic peaks at a diffraction angle $2\theta$ of 10.9, 16.4, and 27.4, for example, an essentially pure crystalline form C (FIG. 7). Further, the powder X-ray diffraction (PXRD) spectrum of crystalline form C may further include characteristic peaks at a diffraction angle $2\theta$ of 5.4, 19.6, 21.9, 24.4, and 33.1, in addition to the previously illustrated peak. Alternatively, crystalline form C may exhibit a powder X-ray diffraction (PXRD) spectrum including characteristic peaks at four or more diffraction angles $2\theta \pm 0.2°$ selected from the group consisting of 5.4, 10.9, 16.4, 19.6, 21.9, 24.4, 27.4, and 33.1.

Crystalline form C has the apex temperature of the endothermic peak within a range of 123° C. to 128° C. during a differential scanning calorimetry (DSC) analysis at a heating rate of 10° C./min (FIG. 8).

Crystalline form C is not a solvate, that is, crystalline form C of Formula 2 is in a non-solvated form. A thermogravimetric analysis (TGA) curve of crystalline form C exhibits a weight loss of less than about 4 wt %, preferably, a weight loss of less than about 2 wt % at about 100° C. or less (FIG. 9).

In yet another embodiment, the present disclosure relates to an amorphous form of a compound 1-(4-benzyloxy-benzyl)-3-methyl-thiourea exhibiting the powder X-ray diffraction (PXRD) spectrum illustrated in FIG. 10.

According to the method for preparing a novel crystal form according to the present disclosure, the novel crystal form is determined depending on a solvent, an anti-solvent, a crystallization method, etc. as used.

Crystalline form A may be prepared from the compound of Formula 2 through slurrying or crystallization using one or more solvents. The solvent used in the crystallization may be selected from the group consisting of diethyl ether, tetrahydrofuran, acetone, N-methyl-2-pyrrolidone, methyl t-butyl ether, water, and a mixed solvent thereof.

In one embodiment, a method for preparing crystalline form A comprises (a) adding 1-(4-benzyloxy-benzyl)-3-methyl-thiourea to a solvent selected from the group consisting of diethyl ether, tetrahydrofuran, acetone, N-methyl-2-pyrrolidone, methyl t-butyl ether, water, and a mixed solvent thereof, to obtain a solution;

(b) stirring or storing the solution to obtain a precipitate; and (c) filtering and washing the precipitate to obtain a 1-(4-benzyloxy-benzyl)-3-methyl-thiourea compound in crystalline form A.

Crystalline form B may be obtained from the compound of Formula 2 using a solvent selected from the group consisting of 1,4-dioxane, acetone, tetrahydrofuran, n-heptane, and a mixed solvent thereof. In one embodiment, a method for preparing crystalline form B comprises:

(a) adding 1-(4-benzyloxy-benzyl)-3-methyl-thiourea to a solvent selected from the group consisting of 1,4-dioxane, acetone, tetrahydrofuran, n-heptane, and a mixed solvent thereof to obtain a solution;

(b) stirring or storing the solution to obtain a precipitate; and (c) isolating a 1-(4-benzyloxy-benzyl)-3-methyl-thiourea compound in crystalline form B from the precipitate.

Crystalline form C may be obtained from the compound of Formula 2 using tetrahydrofuran as a solvent and toluene as an anti-solvent. In one embodiment, a method for preparing crystalline form C comprises:

(a) adding 1-(4-benzyloxy-benzyl)-3-methyl-thiourea to tetrahydrofuran as solvent to obtain a solution;

(b) adding toluene as an anti-solvent to the solution;

(c) evaporating the solution obtained in step (b) to obtain a precipitate; and (d) filtering and washing the precipitate to obtain a 1-(4-benzyloxy-benzyl)-3-methyl-thiourea compound in crystalline form C.

An amorphous form may be obtained using a solvent selected from the group consisting of dimethylamide, N-methyl-2-pyrrolidone, dimethylacetamide, and a mixed solvent thereof. In one embodiment, a method for preparing an amorphous form thereof comprises:

(a) adding 1-(4-benzyloxy-benzyl)-3-methyl-thiourea to a solvent selected from the group consisting of dimethylamide, N-methyl-2-pyrrolidone, dimethylacetamide, and a mixed solvent thereof to obtain a solution; and (b) adding methyl t-butylether to the solution and slurrying the resulting mixture.

In another embodiment, the preparation method comprises:

(a) adding 1-(4-benzyloxy-benzyl)-3-methyl-thiourea to a solvent selected from the group consisting of dimethylamide, N-methyl-2-pyrrolidone, dimethylacetamide, and a mixed solvent thereof to obtain a solution or suspension; and (b) heating, equilibrating, cooling, and evaporating the solution or suspension.

The present disclosure provides a pharmaceutical composition for preventing or treating a metabolic disease or inflammatory disease, comprising 1-(4-benzyloxy-benzyl)-3-methyl-thiourea in crystalline forms A, B, C, or amorphous form; and a pharmaceutically acceptable carrier or excipient. In one embodiment, the present disclosure provides a method for preventing or treating a metabolic disease or inflammatory disease in a subject in need thereof, comprising administering to the subject a therapeutically effective amount of 1-(4-benzyloxy-benzyl)-3-methyl-thiourea in crystalline forms A, B, C, or amorphous form. In another embodiment, the present disclosure provides a use of 1-(4-benzyloxy-benzyl)-3-methyl-thiourea in crystalline forms A, B, C, or amorphous form for preventing or treating a metabolic disease or inflammatory disease.

The compound of 1-(4-benzyloxy-benzyl)-3-methyl-thiourea exhibits therapeutic effect by activating RORα gene. The pharmaceutical composition according to the present disclosure is effective for the prevention or treatment of a metabolic disease and an inflammatory disease, and, particularly, may be used for the prevention or treatment of a liver disease by regulating the homeostasis of cholesterol and suppressing the synthesis of lipids. Preferably, the metabolic disease includes arteriosclerosis or a liver disease, and the liver disease may include fatty liver, alcoholic fatty liver, hyperlipidemia, and the like. In addition, the compound of the present disclosure, which activates RORα gene, may be applied to suppress the formation of an atherosclerotic plaque accompanying the proliferation of vascular smooth muscles and to prevent restenosis caused by the proliferation of vascular smooth muscles after a balloon therapy or a stent.

The present disclosure provides crystalline forms A, B, C, or an amorphous form of 1-(4-benzyloxy-benzyl)-3-methyl-thiourea. In particular, crystalline form A has remarkable physical and chemical properties, such as stability and non-hygroscopic property. Specifically, crystalline form A of 1-(4-benzyloxy-benzyl)-3-methyl-thiourea according to the present disclosure has storage stability over a long period of time, is stable even under an acceleration condition, and is remarkable in physical and chemical properties such as non-hygroscopic property, so that it is possible to expect stability in storage required upon the long-term use when prepared as a pharmaceutical preparation for preventing or treating a metabolic disease or inflammatory disease.

Since the method for preparing the crystalline form of the present disclosure does not require a column purification process through a crystallization process, the method is economically feasible, and thus suitable for industrial production.

Figure 1:
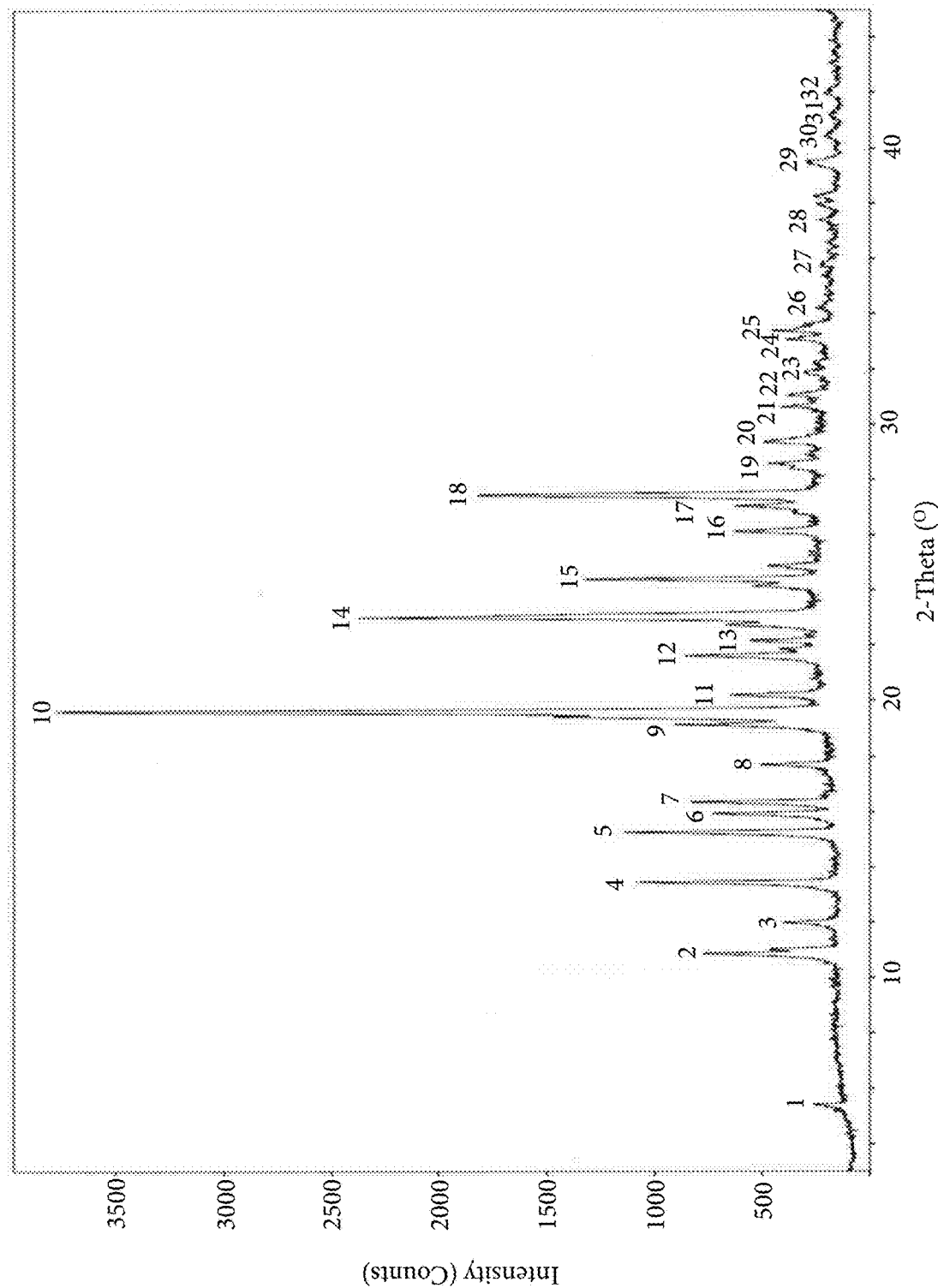
FIG. 1 is a graph illustrating an example of a PXRD pattern of crystalline form A of 1-(4-benzyloxy-benzyl)-3-methyl-thiourea.

Hereinafter, embodiments of the present disclosure will be described in more detail through the working examples. However, the examples are merely provided for a better understanding of the present disclosure for the purpose of illustration, but are not to be construed as the limitation of the claimed scope. Of course, it will be apparent to those skilled in the art that various changes and modifications can be made within the scope and technical scope of the present disclosure, and such changes and modifications also fall within the scope of the appended claims.

EXAMPLES

Preparation Example 1. Preparation of a Compound of Formula 2

A compound of Formula 2, 1-(4-benzyloxy-benzyl)-3-methyl-thiourea, was obtained in a solid form in accordance with the method disclosed in Korean Patent No. 10-1450960 and US 2018/0265462 which are incorporated herein.

$^1$H NMR (600 MHz, DMSO-$d_6$) δ 7.80 (s, 1H), 7.48~7.26 (m, 5H), 7.25~7.20 (d, 2H), 67.0~6.90 (d, 2H), 5.08 (s, 2H), 4.54 (s, 2H), 2.82 (s, 3H)

Example 1. Preparation of Crystalline Form A of Formula 2 using Diethyl Ether (Et2O)

1-(4-benzyloxy-benzyl)-3-methyl-thiourea (2.0 g) was put into 220 mL of Et2O, followed by stirring at room temperature for 6 hours. The product was filtered, and the solid was collected, and then washed with Et2O (10 mL) and dried under vacuum at room temperature overnight to obtain a pure white solid product (1.0 g).

Example 2. Preparation of Crystalline Form A of Formula 2 Using Tetrahydrofuran (THF)/Methyl t-Butyl Ether (MTBE)

1-(4-benzyloxy-benzyl)-3-methyl-thiourea (2.0 g) was dissolved in THF (26 mL) at 15 to 25° C. MTBE (78 mL) was added dropwise to the solution. The reaction solution was evaporated at 15 to 25° C. for 20 hours. While stirring at 15 to 25° C. for another 18 hours, a large amount of precipitate was produced. The precipitate was filtered, washed with MTBE (10 mL), and dried under vacuum at 50° C. overnight to obtain a pure white solid product (0.9 g).

Example 3. Preparation of Crystalline Form A of Formula 2 Using Acetone/Methyl t-Butyl Ether (MTBE)

1-(4-benzyloxy-benzyl)-3-methyl-thiourea (2.0 g) was dissolved in acetone (40 mL). The solution was stirred, and then MTBE was added thereto in an amount of 50 mL at a time until the total amount of MTBE reached 3,200 mL. A clear solution was obtained by stirring at room temperature, and further stirred at 5° C. for 5 days, and then at 20 to 30° C. for 3 days. The solution was concentrated to 150 mL at 40° C., and then cooled to 0 to 5° C., from which a large amount of solid was precipitated. The precipitate was filtered, washed with MTBE (10 mL), and dried under vacuum at 50° C. overnight to obtain a pure white solid product (0.8 g).

Example 4. Preparation of Crystalline Form A of Formula 2 using N-Methyl-2-Pyrrolidone (NMP)/Water 1-(4-benzyloxy-benzyl)-3-methyl-thiourea (2.0 g) was dissolved in 6 mL of NMP. The solution was transferred to a flask containing 8 mL of water. The flask was sealed with a stopper and stored at room temperature for a time sufficient for the solvent vapor to react with the solution. After diffusion of the vapor-solution, a clear solution was obtained and evaporated at 50° C. for 10 hours. A white solid was slightly produced, and filtered. The filtered cake was washed with water (10 mL), and dried under vacuum at 50° C. overnight to obtain a pure white solid product (0.8 g).

Example 5. Preparation of Crystalline Form B of Formula 2 using 1,4-Dioxane/n-Heptane 1-(4-benzyloxy-benzyl)-3-methyl-thiourea (14.9 mg) was dissolved in 0.3 mL of 1,4-dioxane in a 20-mL glass vial. The solution was stirred, and then n-heptane was added thereto in an amount of 100 μL at a time until a precipitate appeared (total volume of n-heptane: 0.6 mL). The precipitate was observed and an obtained solid was isolated.

Example 6. Preparation of Crystalline Form B of Formula 2 using Acetone/n-Heptane 1-(4-benzyloxy-benzyl)-3-methyl-thiourea (15.1 mg) was dissolved in 0.3 mL of acetone in a 3-mL glass vial. The sample was stirred while adding the solution dropwise to 5.0 mL of n-heptane at room temperature. The precipitate was observed and an obtained solid was isolated.

Example 7. Preparation of Crystalline Form B of Formula 2 using Tetrahydrofuran (THF)/n-Heptane 1-(4-benzyloxy-benzyl)-3-methyl-thiourea (15.0 mg) was dissolved in 0.2 mL of THF in a 3-mL glass vial. The sample was stirred while adding the solution dropwise to 5.0 mL of n-heptane at room temperature. The precipitate was observed, and the obtained product was isolated for PXRD analysis.

Example 8. Preparation of Crystalline Form B of Formula 2 Using Acetone 1-(4-benzyloxy-benzyl)-3-methyl-thiourea (15.0 mg) was dissolved in 0.4 mL of acetone in a 3-mL glass vial. The solution was filtered with a PTFE membrane (pore size of 0.45 μm), and the filtrate was used in the next step. The visually clear solution was evaporated at room temperature, and the vial was sealed with Parafilm® (poked with 5 pin-holes). After evaporated for 9 days, the obtained solid was isolated.

Example 9. Preparation of Crystalline Form C of Formula 2 Using Tetrahydrofuran (THF)/Toluene 1-(4-benzyloxy-benzyl)-3-methyl-thiourea (2.0 g) was dissolved in THF (26 mL) at 15 to 25° C. Toluene (528 mL) was added dropwise to the solution. The reaction solution was evaporated at 15 to 25° C. for 5 days, concentrated to 50 mL at 50° C., and then cooled to 0 to 5° C. A large amount of precipitate was produced and filtered. The filtered cake was washed with toluene (10 mL), and dried under vacuum at 50° C. overnight to obtain a pure white solid product (1.3 g).

Example 10. Preparation of Amorphous Form of Formula 2 Using Dimethylacetamide (DMAC)/Methyl t-Butyl Ether (MTBE)

1-(4-benzyloxy-benzyl)-3-methyl-thiourea (14.9 mg) was dissolved in 0.1 mL of DMAC in a 3-mL glass vial. The API solution was added dropwise to 5.0 mL of MTBE at room temperature while stirring the sample. A clear solution was obtained by stirring at room temperature, and then the solution was transferred, slurried at 5° C. for about 9 days, and evaporated at room temperature for about 3 days.

Example 11. Preparation of Amorphous Form of Formula 2 using N-Methyl-2-Pyrrolidone (NMP)/Methyl t-Butyl Ether (MTBE)

1-(4-benzyloxy-benzyl)-3-methyl-thiourea (14.9 mg) was dissolved in 0.1 mL of NMP in a 3-mL glass vial. The solution was added dropwise to 5.0 mL of MTBE at room temperature while stirring the sample. A clear solution was obtained by stirring at room temperature, and then the solution was transferred, slurried at 5° C. for about 9 days, and evaporated at room temperature for about 3 days.

Experimental Example 1. Powder X-Ray Diffraction (PXRD) Spectrum

The crystalline forms and amorphous form of 1-(4-benzyloxy-benzyl)-3-methyl-thiourethane prepared in the examples were measured by a powder X-ray diffraction device, and representative data are illustrated in FIGS. 1, 4, 7, and 10.

Figure 4:
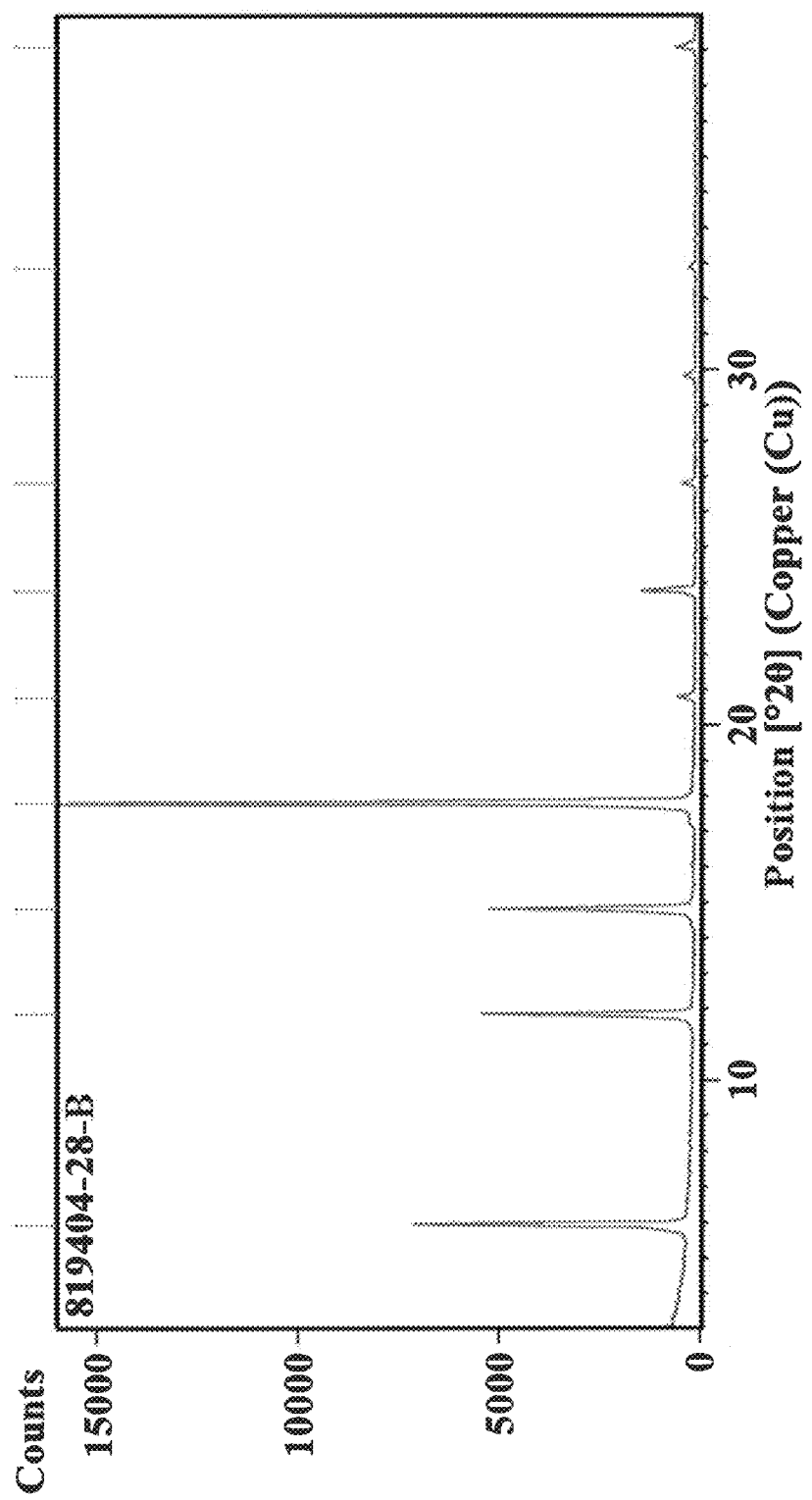
FIG. 4 is a graph illustrating an example of a PXRD pattern of crystalline form B of 1-(4-benzyloxy-benzyl)-3-methyl-thiourea.
Figure 7:
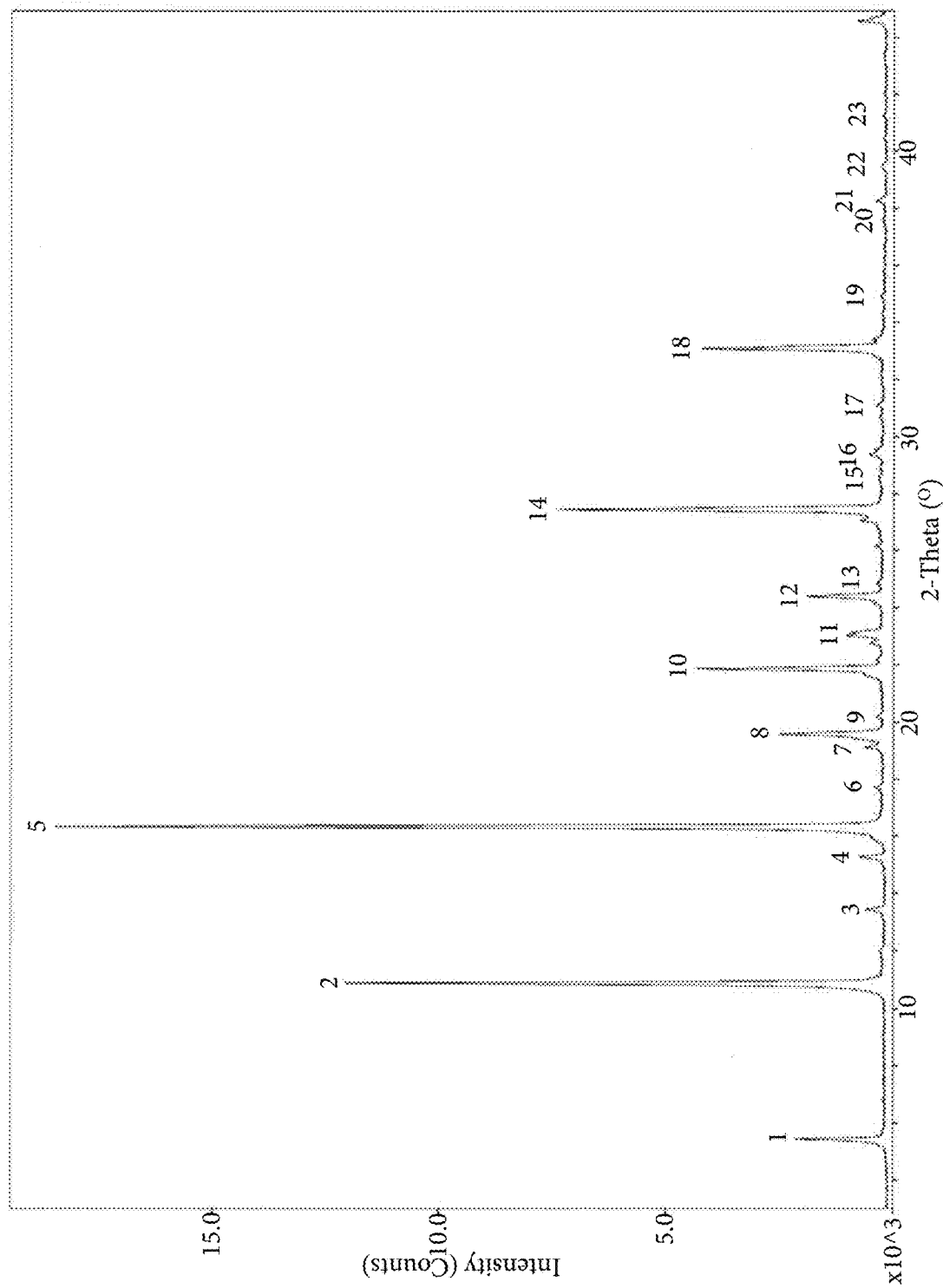
FIG. 7 is a graph illustrating an example of a PXRD pattern of crystalline form C of 1-(4-benzyloxy-benzyl)-3-methyl-thiourea.

As confirmed from FIGS. 1, 4, and 7, the diffraction angle 2θ value exhibiting a characteristic peak for each crystalline form are as follows.

Crystalline Form A: 10.9, 13.5, 15.3, 16.0, 16.4, 19.7, 21.7, 23.1, 24.5, 27.1, 27.5, and 29.5

Crystalline Form B: 5.9, 11.8, 14.8, 17.8, and 23.8

Crystalline Form C: 5.4, 10.9, 16.4, 19.6, 21.9, 24.4, 27.4, and 33.1

Experimental Example 2. Differential Scanning Calorimetry (DSC) Spectrum

Figure 2:
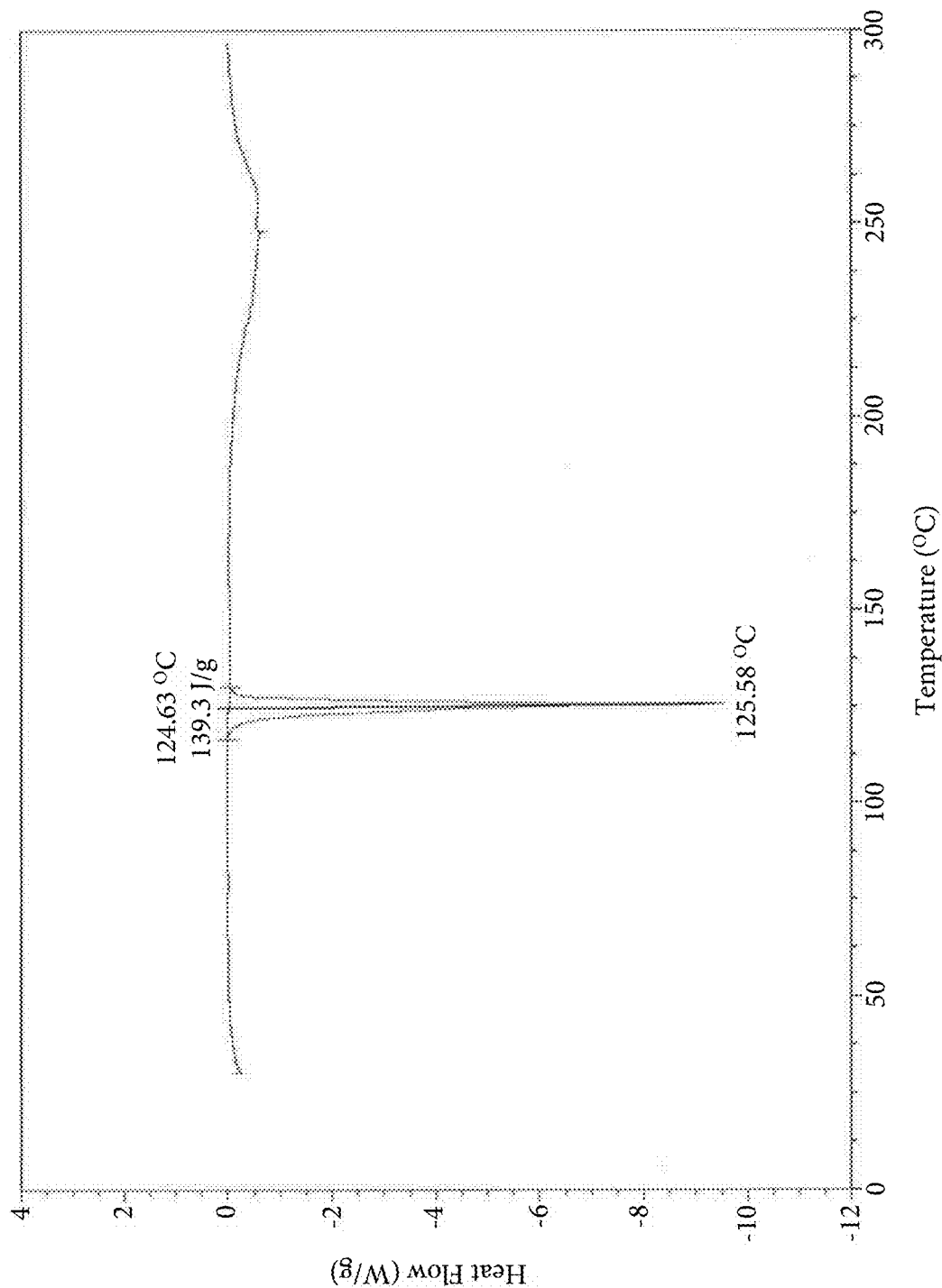
FIG. 2 is a graph illustrating an example of an endothermic peak during a DSC analysis of crystalline form A of 1-(4-benzyloxy-benzyl)-3-methyl-thiourea.
Figure 3:
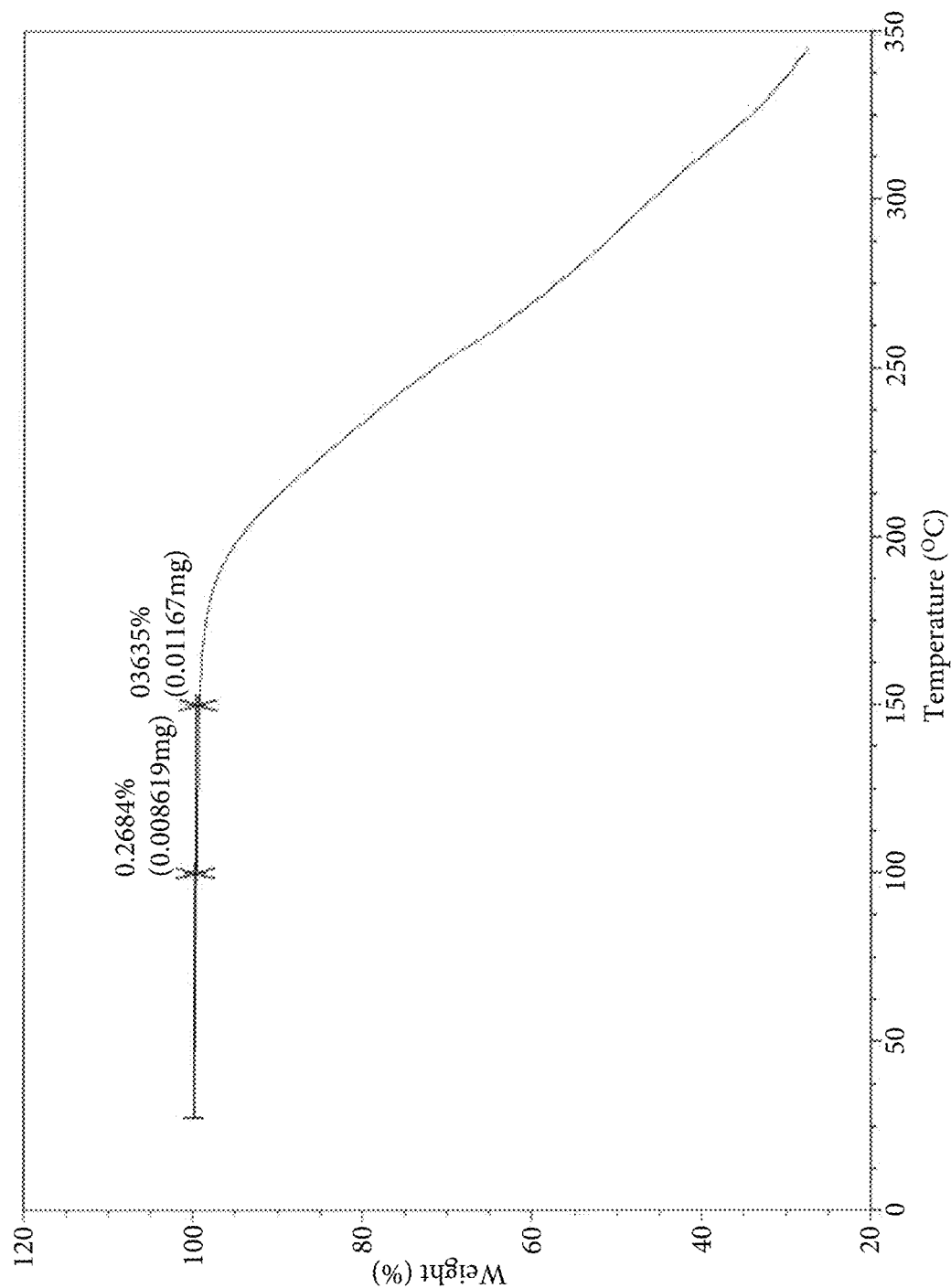
FIG. 3 is a graph illustrating an example of a TGA curve of crystalline form A of 1-(4-benzyloxy-benzyl)-3-methyl-thiourea.
Figure 5:
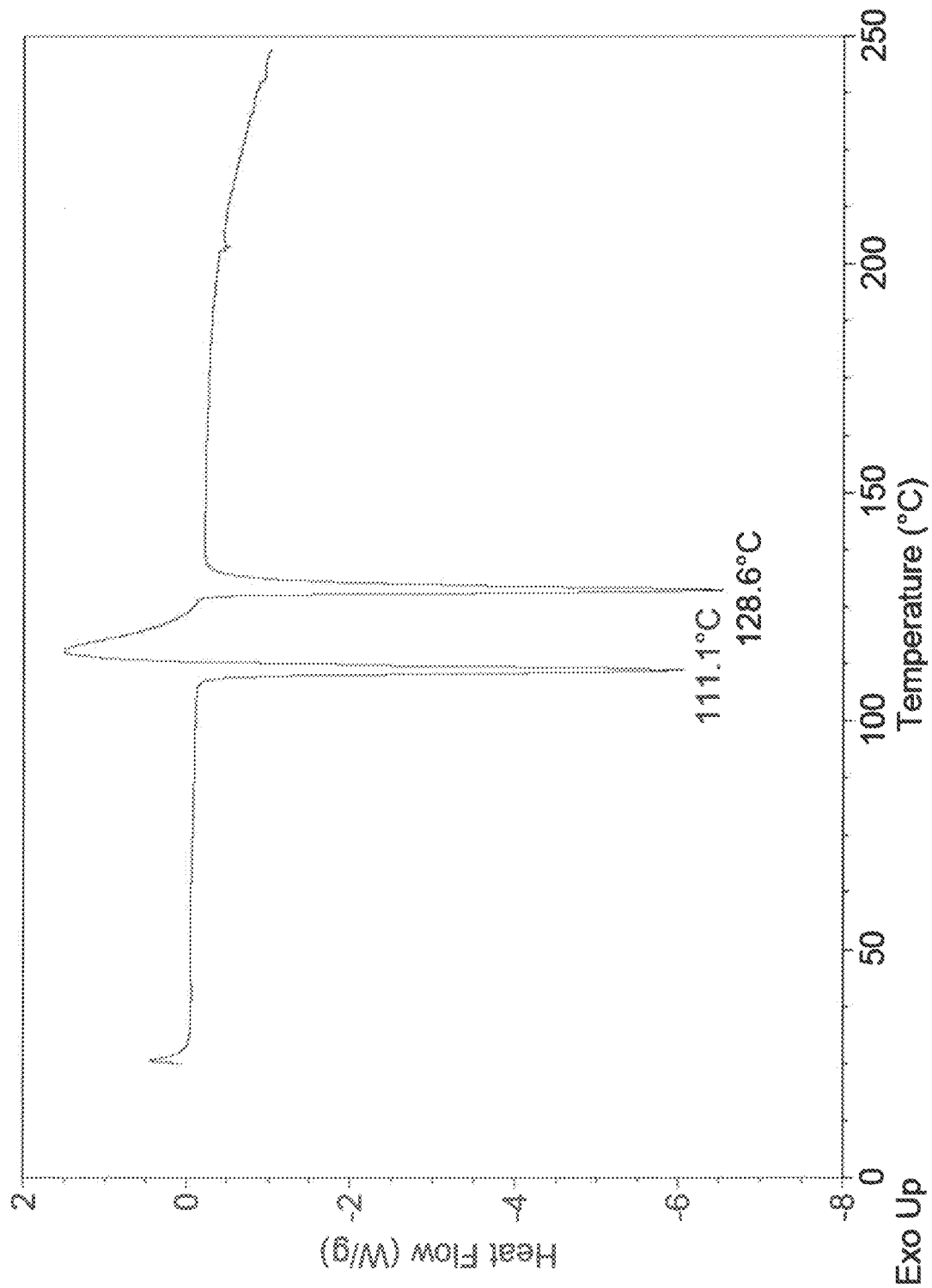
FIG. 5 is a graph illustrating an example of an endothermic peak during a DSC analysis of crystalline form B of 1-(4-benzyloxy-benzyl)-3-methyl-thiourea.
Figure 6:
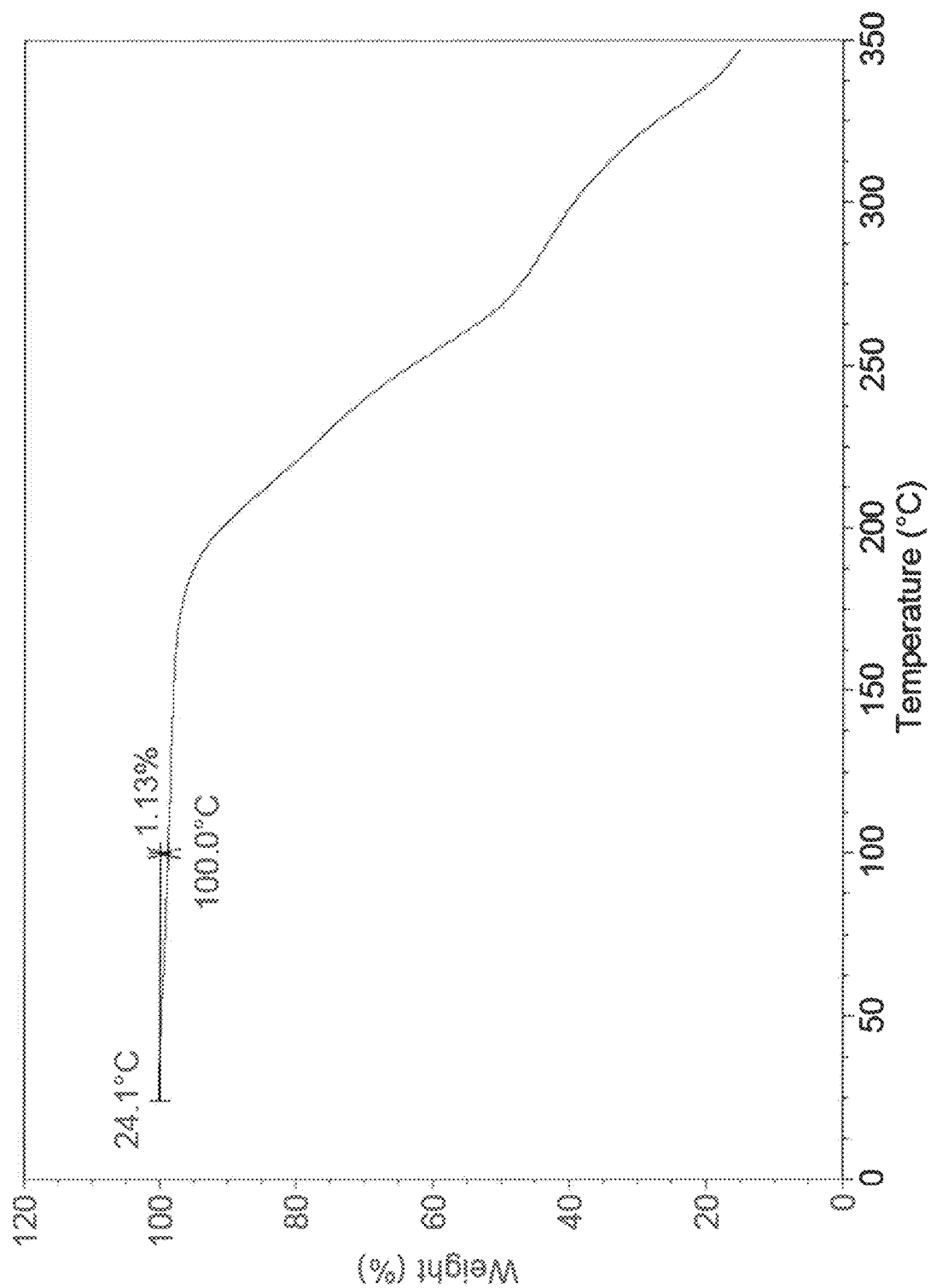
FIG. 6 is a graph illustrating an example of a TGA curve of crystalline form B of 1-(4-benzyloxy-benzyl)-3-methyl-thiourea.
Figure 8:
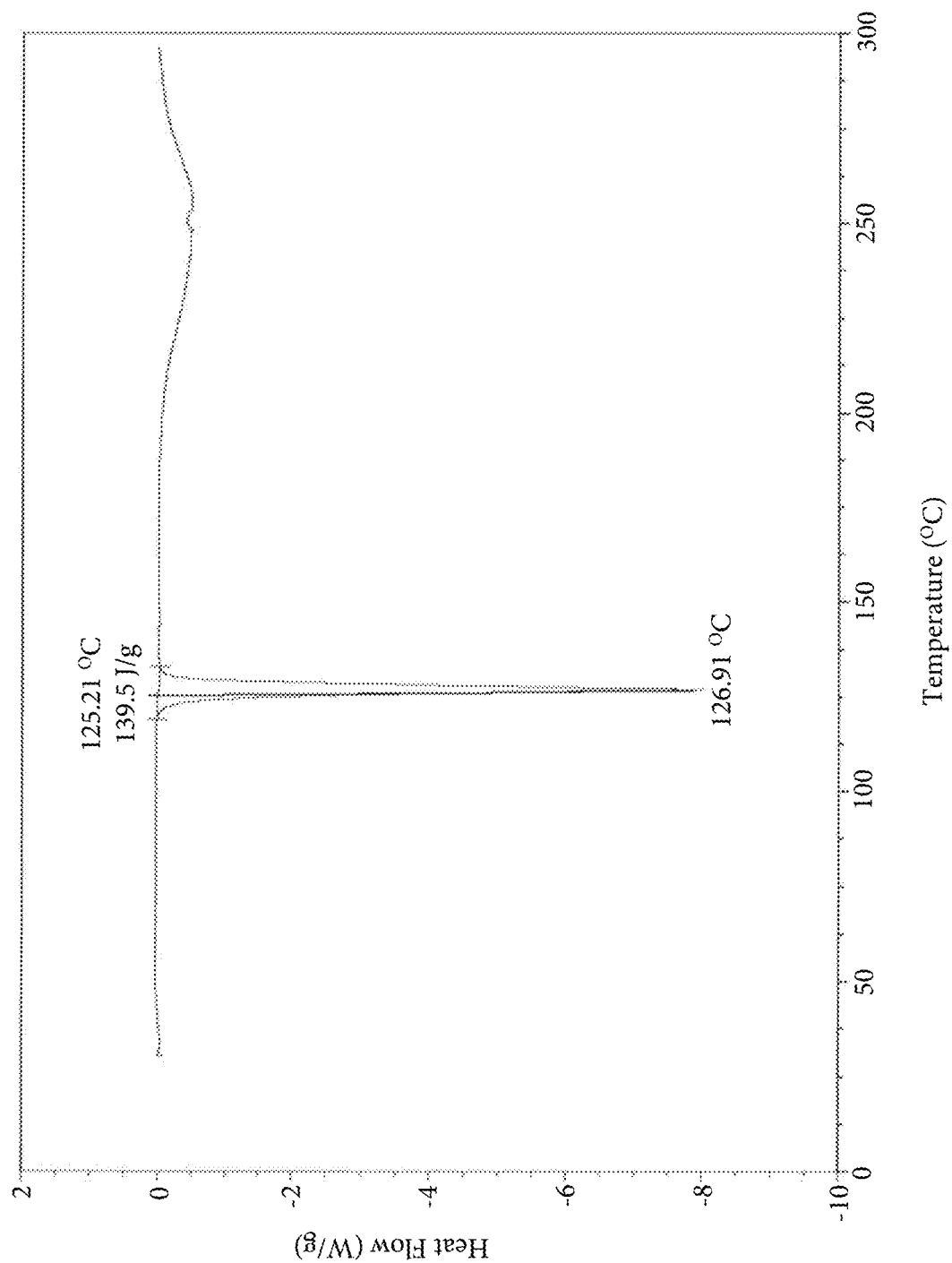
FIG. 8 is a graph illustrating an example of an endothermic peak during a DSC analysis of crystalline form C of 1-(4-benzyloxy-benzyl)-3-methyl-thiourea.
Figure 9:
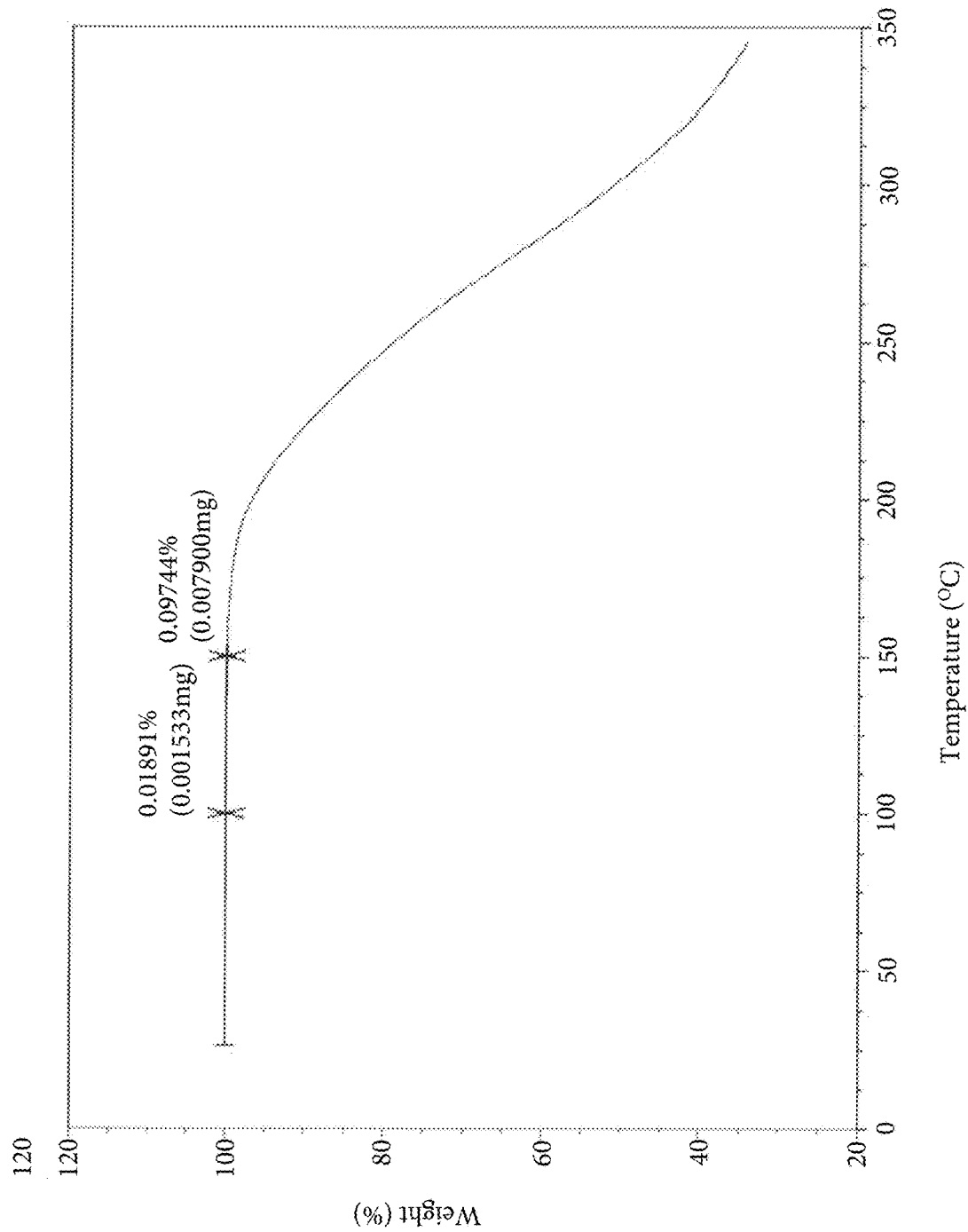
FIG. 9 is a graph illustrating an example of a TGA curve of crystalline form C of 1-(4-benzyloxy-benzyl)-3-methyl-thiourea.
Figure 10:
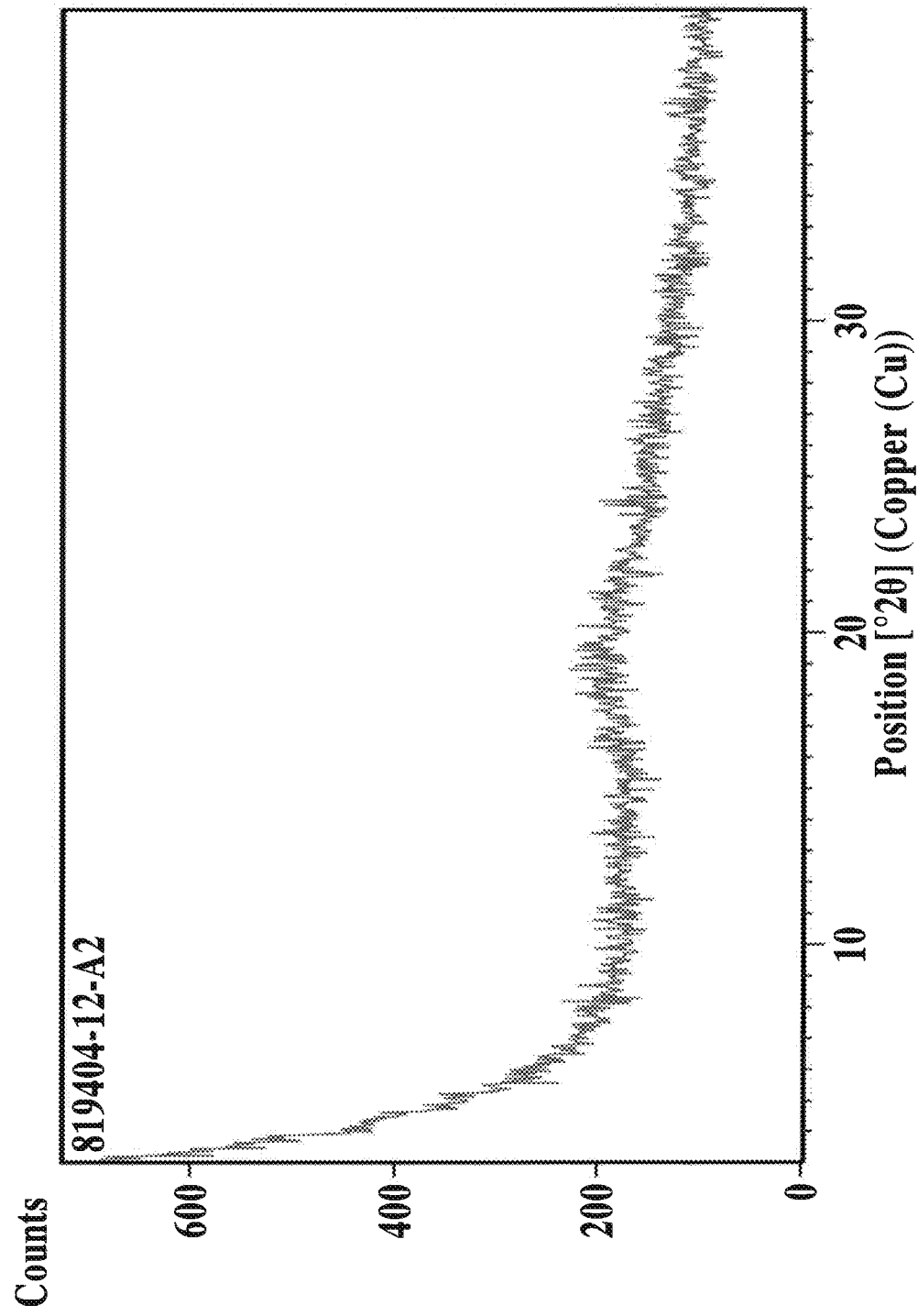
FIG. 10 is a graph illustrating an example of a PXRD pattern of an amorphous compound of 1-(4-benzyloxy-benzyl)-3-methyl-thiourea.

The crystalline forms A, B, and C of 1-(4-benzyloxy-benzyl)-3-methyl-thiourea prepared in the examples were measured by a differential scanning calorimetry device, and representative data (endothermic peaks) obtained therefrom are illustrated in FIGS. 2, 5, and 8.

Experimental Example 3. Hygroscopicity Test Through Dynamic Vapor Sorption (DVS)

From a pharmaceutical point of view, it is desired to maintain the initial moisture and morphology without absorbing moisture even in a moisture environment. As a result of evaluating the hygroscopicity of the crystalline forms prepared in the examples through a DVS analyzer, it was confirmed that crystalline form A contains less moisture under 80% moisture condition than crystalline form B.

TABLE 1

| Crystalline form | Hygroscopicity (25° C./80% RH) | Morphology Change |
|---|---|---|
| Crystalline form A | 0.07% | No |
| Crystalline form B | 0.20% | No |

Experimental Example 4. Stability Test

From a pharmaceutical point of view, the stability of an active ingredient is very important. It is not preferable pharmaceutically that impurities are excessively produced or the crystalline form is changed under a storage condition. It was confirmed that for both crystalline forms A and B, impurities were not increased under given conditions, but crystalline form B was being changed into crystalline form A under storage condition at room temperature, and was all changed into crystalline form A under an acceleration condition.

TABLE 2

| Crystalline form | Condition | Time | Final crystalline form | HPLC Purity (area %) |
|---|---|---|---|---|
| Crystalline form A | Initial | — | — | 99.55 |
| | 25° C./60% RH | 1 week | Crystalline form A | 99.71 |
| | 40° C./75% RH | | Crystalline form A | 99.66 |
| Crystalline form B | Initial | — | — | 99.49 |
| | 25° C./60% RH | 1 week | Crystalline forms A + B | 99.70 |
| | 40° C./75% RH | | Crystalline form A | 99.72 |

Experimental Example 5. Stability Test Under Storage Condition

From a pharmaceutical point of view, the stability of an active ingredient is very important. It is not preferable pharmaceutically that impurities are excessively produced or the crystalline form is changed under a storage condition. As a result of evaluating the stability of crystalline form A under storage conditions at room temperature, it could be confirmed that since impurities were not increased and the crystalline form was not changed, crystalline form A is a very stable material.

TABLE 3

| | Initial | 1 month | 3 months | 6 months |
|---|---|---|---|---|
| Purity (%) | 100.0 | 100.0 | 100.0 | 100.0 |
| Crystalline form | Crystalline form A | Crystalline form A | Crystalline form A | Crystalline form A |

The invention claimed is:

1. A 1-(4-benzyloxy-benzyl)-3-methyl-thiourea compound in crystalline form A, characterized in exhibiting a powder X-ray diffraction (PXRD) spectrum comprising characteristic peaks at four or more diffraction angles 2θ±0.2° selected from the group consisting of 10.9, 13.5, 15.3, 16.0, 16.4, 19.7, 21.7, 23.1, 24.5, 27.1, 27.5, and 29.5.

2. The 1-(4-benzyloxy-benzyl)-3-methyl-thiourea compound in crystalline form A according to claim 1, characterized in having an endothermic peak within a range of 120°

C. to 130° C. during a differential scanning calorimetry (DSC) analysis at a heating rate of 10° C./min.

3. The 1-(4-benzyloxy-benzyl)-3-methyl-thiourea compound in crystalline form A according to claim 1, characterized in that a thermogravimetric analysis (TGA) curve exhibits a weight loss of less than 4 wt % at 100° C. or less, and the compound is in a non-solvated form.

4. A 1-(4-benzyloxy-benzyl)-3-methyl-thiourea compound in crystalline form B, characterized in exhibiting a powder X-ray diffraction (PXRD) spectrum comprising characteristic peaks at four or more diffraction angles 2θ±0.2° selected from the group consisting of 5.9, 11.8, 14.8, 17.8, and 23.8.

5. The 1-(4-benzyloxy-benzyl)-3-methyl-thiourea compound in crystalline form B according to claim 4, characterized in having an endothermic peak within a range of 105° C. to 115° C. and a range of 123° C. to 130° C. during a differential scanning calorimetry (DSC) analysis at a heating rate of 10° C./min.

6. The 1-(4-benzyloxy-benzyl)-3-methyl-thiourea compound in crystalline form B according to claim 4, characterized in that a thermogravimetric analysis (TGA) curve exhibits a weight loss of less than 4 wt % at 100° C. or less, and the compound is in a non-solvated form.

7. A 1-(4-benzyloxy-benzyl)-3-methyl-thiourea compound in crystalline form C, characterized in exhibiting a powder X-ray diffraction (PXRD) spectrum comprising characteristic peaks at four or more diffraction angles 2θ±0.2° selected from the group consisting of 5.4, 10.9, 16.4, 19.6, 21.9, 24.4, 27.4, and 33.1.

8. The 1-(4-benzyloxy-benzyl)-3-methyl-thiourea compound in crystalline form C according to claim 7, characterized in having an endothermic peak within a range of 123° C. to 128° C. during a differential scanning calorimetry (DSC) analysis at a heating rate of 10° C./min.

9. The 1-(4-benzyloxy-benzyl)-3-methyl-thiourea compound in crystalline form C according to claim 7, characterized in that a thermogravimetric analysis (TGA) curve exhibits a weight loss of less than 4 wt % at 100° C. or less, and the compound is in a non-solvated form.

10. A method for preparing the 1-(4-benzyloxy-benzyl)-3-methyl-thiourea compound in crystalline form A according to claim 1, which comprises:

(a) adding 1-(4-benzyloxy-benzyl)-3-methyl-thiourea to a solvent selected from the group consisting of diethyl ether, tetrahydrofuran, acetone, N-methyl-2-pyrrolidone, methyl t-butyl ether, water, and a mixed solvent thereof, to obtain a solution;
(b) stirring or storing the solution to obtain a precipitate; and
(c) filtering and washing the precipitate to obtain a 1-(4-benzyloxy-benzyl)-3-methyl-thiourea compound in crystalline form A.

11. A method for preparing the 1-(4-benzyloxy-benzyl)-3-methyl-thiourea compound in crystalline form B according to claim 4, which comprises:

(a) adding 1-(4-benzyloxy-benzyl)-3-methyl-thiourea to a solvent selected from the group consisting of 1,4-dioxane, acetone, tetrahydrofuran, n-heptane, and a mixed solvent thereof to obtain a solution;
(b) stirring or storing the solution to obtain a precipitate; and
(c) isolating a 1-(4-benzyloxy-benzyl)-3-methyl-thiourea compound in crystalline form B from the precipitate.

12. A method for preparing the 1-(4-benzyloxy-benzyl)-3-methyl-thiourea compound in crystalline form C according to claim 7, which comprises:

(a) adding 1-(4-benzyloxy-benzyl)-3-methyl-thiourea to tetrahydrofuran as solvent to obtain a solution;
(b) adding toluene as an anti-solvent to the solution;
(c) evaporating the solution obtained in step (b) to obtain a precipitate; and
(d) filtering and washing the precipitate to obtain a 1-(4-benzyloxy-benzyl)-3-methyl-thiourea compound in crystalline form C.

13. A pharmaceutical composition comprising the 1-(4-benzyloxy-benzyl)-3-methyl-thiourea compound in crystalline form A according to claim 1; and a pharmaceutically acceptable carrier or excipient.

14. A method for preventing or treating a metabolic disease or inflammatory disease, the method comprising administering the pharmaceutical composition according to claim 13.

15. The method according to claim 14, wherein the metabolic disease is arteriosclerosis, fatty liver, alcoholic fatty liver, or hyperlipidemia.

* * * * *